United States Patent
Hochgraeber et al.

(10) Patent No.: US 9,939,415 B2
(45) Date of Patent: Apr. 10, 2018

(54) HIGH-PRESSURE CONTROL VALVE FOR HIGH-PERFORMANCE LIQUID CHROMATOGRAPHY

(71) Applicant: DIONEX SOFTRON GMBH, Germering (DE)

(72) Inventors: Hermann Hochgraeber, Offenberg-Heuhausen (DE); Joachim Wiechers, Planegg (DE); Adolf Satzinger, Olching (DE)

(73) Assignee: DIONEX SOFTRON GMBH, Germering (DE)

( * ) Notice: Subject to any disclaimer, the term of this patent is extended or adjusted under 35 U.S.C. 154(b) by 0 days.

(21) Appl. No.: 15/625,691

(22) Filed: Jun. 16, 2017

(65) Prior Publication Data
US 2017/0284980 A1    Oct. 5, 2017

Related U.S. Application Data

(63) Continuation-in-part of application No. 13/979,407, filed as application No. PCT/DE2011/075325 on Dec. 29, 2011, now abandoned.

(30) Foreign Application Priority Data

Jan. 12, 2011 (DE) .................. 10 2011 000 104

(51) Int. Cl.
*G01N 30/20* (2006.01)
*F16K 11/076* (2006.01)
*G01N 30/22* (2006.01)

(52) U.S. Cl.
CPC ............ *G01N 30/20* (2013.01); *F16K 11/076* (2013.01); *G01N 30/22* (2013.01);
(Continued)

(58) Field of Classification Search
CPC ............. G01N 30/20; G01N 2030/202; G01N 2030/201; G01N 2030/204; G01N 30/22;
(Continued)

(56) References Cited

U.S. PATENT DOCUMENTS 4,235,416 A * 11/1980 LaCoste ................. F16K 1/482
251/86
4,444,066 A    4/1984 Ogle et al.
(Continued)

FOREIGN PATENT DOCUMENTS

CN    101680861    3/2010
CN    101849126    9/2010
(Continued)

OTHER PUBLICATIONS

Advanced Instrumental Analysis Experiment and Technology, 2 pages, Feb. 28, 2006.
(Continued)

*Primary Examiner* — Michael R Reid

(57) ABSTRACT

A high-pressure switching valve includes a stator and a rotor. The stator includes a plurality of ports where each port is connected at one end to a port connection and having at another end a predetermined port opening cross section at a stator end face of the stator. The rotor includes a rotor end face and at least one or a plurality of grooves. The rotor can be configured to have a rotary position with respect to the stator where two predetermined port opening cross sections connect to one of the grooves in a pressure-tight manner. The rotor and the stator can be pressed together in a sealing manner at the rotor end face and the stator end face in regions away from the port opening cross sections and the at least one or a plurality of grooves. The rotor and the stator each include a hard material. The rotor can be configured to wobble or tilt with respect to a rotational axis of the rotor.

20 Claims, 6 Drawing Sheets

(52) U.S. Cl.
CPC . *G01N 2030/201* (2013.01); *G01N 2030/202* (2013.01); *G01N 2030/204* (2013.01)

(58) Field of Classification Search
CPC .......... F16K 11/076; F16K 3/08; F16K 3/085; F16K 11/074; F16K 11/0743; F16K 27/045
USPC .............. 137/625.4, 625.46, 625.17, 625.41; 251/84–88
See application file for complete search history.

(56) References Cited

U.S. PATENT DOCUMENTS

| | | | |
|---|---|---|---|
| 4,580,759 | A | 4/1986 | Leaseburge et al. |
| 5,920,006 | A | 7/1999 | Zelechonok |
| 8,225,817 | B2 | 7/2012 | Wilen |
| 8,236,175 | B2 | 8/2012 | Maeda et al. |
| 8,322,374 | B2 | 12/2012 | Tomita |
| 2001/0035516 | A1 | 11/2001 | Nichols et al. |
| 2010/0276617 | A1* | 11/2010 | Yasunaga ............ F16K 11/0743 251/129.11 |
| 2010/0281959 | A1 | 11/2010 | Berndt |

FOREIGN PATENT DOCUMENTS

| | | |
|---|---|---|
| CN | 101896750 A | 11/2010 |
| JP | 2004324890 | 11/2004 |
| JP | 2008215494 | 9/2008 |
| WO | 2011001460 | 1/2011 |

OTHER PUBLICATIONS

Heaton et al., "Use of modifier as trapping fluid in preparative supercritical fluid chromatography," J of Chromatography A, 753, 306-311, 1996.

Research progress of ultrahigh-pressure liquid chromatograph and the related issues caused by ultrahigh-pressure, 7 pages, Jan. 31, 2008.

Wu et al., "Practical aspects of ultrahigh pressure capillary liquid chromatography," J. of Chromatography A, 911, 1-12, 2001.

* cited by examiner

HIGH-PRESSURE CONTROL VALVE FOR HIGH-PERFORMANCE LIQUID CHROMATOGRAPHY

CROSS-REFERENCES TO RELATED APPLICATIONS

This application is a Continuation-in-Part of U.S. patent application Ser. No. 13/979,407 filed Jul. 12, 2013 and entitled HIGH-PRESSURE CONTROL VALVE FOR HIGH-PERFORMANCE LIQUID CHROMATOGRAPHY, which is a National Stage of International Patent Application No. PCT/DE2011/075325 filed Dec. 29, 2011 and published as WO 2012/095097 on Jul. 19, 2012, which claims priority to German Patent Application No. 10 2011 000 104.2 filed Jan. 12, 2011, the entire contents of which applications is incorporated herein for all purposes by this reference.

FIELD OF THE INVENTION

The invention relates to a high-pressure switching valve for high-performance liquid chromatography (HPLC).

BACKGROUND

In HPLC, a sample to be investigated has to be fed into a high-pressure liquid stream, wherein the latter should only be interrupted for as short a period of time as possible. For this purpose, high-pressure switching valves in the form of high-pressure injection valves are used which allow virtually interruption-free switching of the liquid stream. Such a structure is described for example in U.S. Pat. No. 3,530,721, the original application for which dates back to as early as 1965.

The further development of such an injection valve is mentioned for example in U.S. Pat. No. 4,242,909. The basic principle of the valve shown therein has become largely established in the meantime in HPLC. Since the present invention is based on this valve type, the principle is explained in more detail in the following text.

FIG. 1 shows a schematic illustration of such a high-pressure valve according to the prior art. It consists of a stator 112 and a rotor 106. The stator 112 has a total of six input and output ports 118. Via these ports, the injection valve can be connected to the other functional elements of the HPLC system via capillary connections. The port connections and high-pressure screw connections required for this purpose are not illustrated in FIG. 1 for the sake of clarity. Within the valve, the ports are in the form of ducts, for example in the form of holes, which lead to the stator end face 114 of the stator 1. In contrast to the simplified illustration in the drawings, in the case of valves produced in practice, the pitch circle diameter on the side of the port connections is usually larger than on the stator end face 114. The rotor has a number of arcuate grooves 108 which are oriented precisely with the holes in the input and output ports or the port opening cross sections thereof in the stator end face 114. This is indicated in FIG. 1 by way of dotted lines. In order to provide a clearer illustration, the rotor 106 is shown at a distance from the stator 112 in FIG. 1. In the assembled state of the valve, this distance is zero, and therefore the surface 110 of the rotor 106 lies directly against the stator end face 114 of the stator 112, as is shown in FIG. 2.

At this point, it should be mentioned that the valve according to FIG. 1 can of course also be used for other purposes than for the purpose of injection.

FIG. 2 shows a schematic illustration of an operationally assembled valve according to the prior art. The rotor 106 is pressed against the stator 112 with a pressure force which is indicated by the arrow F, such that a common interface 110 is formed between the rotor 106 and the stator 112, the two parts sealing against one another at said interface 110. The pressure force F is in this case measured such that the arrangement is still sealed even at the highest pressures to be expected.

In the first switching position, shown in FIG. 1 and FIG. 2, of the valve, the grooves 108 are oriented with respect to the port opening cross sections of the input and output ports 118 such that they produce three connections between in each case two adjacent input and output ports. On account of the sealing action at the interface or contact face between the rotor 106 and the stator 112, liquid supplied to a port 118 can thus emerge only at the relevant adjacent port 118.

In order to switch the valve into a second switching position, the rotor 106 can be rotated through 60° with respect to the stator 112 such that the grooves now connect together in each case those ports which previously had no connection. The direction of rotation is indicated in FIG. 1 by an arrow on the rotor. However, the direction of rotation can also to be selected to be in the opposite direction.

Switching is usually executed by a motor-powered drive which can rotate the rotor 106 with respect to the stator 112. For the sake of clarity, the drive has been omitted in the drawings. In principle, switching of the valve can also take place manually, however.

The advantage of such valves is that they can be used for very high pressures, given a sufficiently high-pressure force F. Furthermore, the holes in the ports 118 can be arranged such that the ends lie on a circle with a very small radius. The grooves then likewise lie on a circle with a very small radius such that the dead volumes of the valve can be kept very small.

In HPLC, a trend toward separation columns having a small particle size has been observed in recent years. Such separation columns allow an improved separation performance and more rapid separation, for which reason the expression fast HPLC is used.

Since the flow resistance increases very greatly as the particle size drops, considerably higher pressures are necessary for fast HPLC. The maximum column pressure that occurs is typically between 100 and 400 bar in conventional HPLC, while 600 to 700 bar are usually necessary in fast HPLC, sometimes even over 1000 bar. A trend toward columns with an even better separation performance is already being observed, said columns requiring even higher pressures of up to about 2000 bar.

In order to be able to operate high-pressure injection valves at such high pressures, the pressure force F (see FIG. 2) has to be increased in a corresponding manner, in order that the valve is sealed. In order that the rotor, which is normally produced from plastics material for cost and technical reasons, can withstand this force, glass- or carbon-fiber-reinforced plastics materials are used according to the prior art. Furthermore, the increased pressure force F results in increased material stress and consequently excessive wear, such that the service life of the valve (number of switching cycles) is unsatisfactory.

This problem can be solved by an appropriate material selection or coating. Thus, a special coating which allows cost-effective production of rotor and stator and at the same time greatly reduces the wear of the materials is described in U.S. Pat. No. 6,453,946.

WO 2009/101695 describes a switching valve in which the stator is provided with a coating made of amorphous carbon (DLC coating) in order to improve stability. The end face or contact surface of the rotor consists of a synthetic resin.

However, it has been shown that although such improved valves behave more favorably, during operation at very high pressures, they nevertheless fail even after a relatively small number of switching cycles.

US 2010/0281959 A1 describes a switching valve suitable for high pressures, wherein the stator and/or rotor surfaces are provided with a DLC layer, wherein an adhesive layer is provided between each particular main body, which can consist of metal. However, when hard material is used in each case for the rotor and the stator, there is the risk that increased wear will occur on account of irregular surface pressure at the contact face, since hard main bodies scarcely deform at the contact face.

Therefore, it is the object of the invention to create a high-pressure switching valve for high-performance liquid chromatography, which has improved wear resistance and stability and can nevertheless be produced in an easy and cost-effective manner.

SUMMARY

The invention is based on the finding that, unlike the conventional structure of such high-pressure switching valves, not only the stator is produced from a hard material but also the rotor. Suitable materials which are highly wear-resistant are in this case in particular metal, ceramic materials and glass. On account of the necessary high-pressure forces, such hard materials have not hitherto been used for the rotor and stator, since the high surface pressure at the contact face of the two parts can result in damage to the surfaces or even to breakage of the rotor or stator even at low manufacturing tolerances of the surfaces or slight incorrect positioning of the surfaces with respect to one another (e.g. in the event of tilting).

According to the invention, it is sufficient in this case if at least those regions of the rotor and stator at which the contact faces or end faces are formed consist of a hard material. Thus, the rotor and/or stator can also have parts made of a corresponding material, in particular insert parts on which the relevant end face is formed.

On account of the mounting of the stator or rotor, or of a relevant part connected thereto, with wobbling or tilting action according to the invention, it is possible to ensure that, in spite of the use of hard materials, a relative uniform surface pressure within the contact face is achieved during the rotary movement of the rotor, but in any case that the rotor end face 110 closely abuts the stator end face, wherein the hard materials ensure much improved wear resistance and stability.

Mounting the rotor with wobbling action with respect to the stator should be understood as meaning that a wobbling movement of the respective element about the rotational axis of the stator or about the axis of the valve takes place. Of course, as a result of the wobbling movement being allowed, the rotor and stator abut one another in every angular position of rotation, wherein a relatively uniform surface pressure over the entire abutment surface, but at least a surface pressure which is rotationally symmetrical about the axis, is additionally achieved.

According to one configuration of the invention, the rotor or the element connected to the rotor is mounted with wobbling action by means of at least one cushion-like element made of a material which is sufficiently soft and elastic to allow the wobbling movement and is also sufficiently rigid to generate the pressure force necessary for the sealing action. A suitable material is, for example, a polymer material, polyimide, polyamideimide or polyether ketone, in particular PEEK.

Rather than mounting the rotor with wobbling or tilting action, the stator can also be mounted in a corresponding manner. Since the contact face between the rotor and stator is located close to the rotational axis of the rotor, the stator has to be mounted radially outside this region, for example in that the stator end face or other faces of the stator which face the rotor rest on an annular element or on a plurality of cushion-like elements distributed around the circumference, said element or elements consisting of a suitable flexible material.

When the rotor is mounted with wobbling action, i.e. is mounted such that wobbling movements of the rotor are allowed, the at least one cushion-like element can be accommodated in an element or part of the drive for the rotor, said element or part being arranged on the side remote from the rotor end face.

In this case, it is appropriate to provide the at least one cushion-like element on or in an element or part of the drive which is driven in rotation and is coupled to the rotor for conjoint rotation. As a result, relative movements in the interface between the cushion-like element and the rotor do not occur or occur only to a very slight extent. At most, the wobbling or tilting movements of the rotor during its rotation can result here in such movements between the rotor and the cushion-like element which, however, are so slight that wear, in particular at the surface of the cushion-like element, can scarcely be expected.

That part of the drive that accommodates the at least one cushion-like element can have a plurality of engagement elements, preferably in the form of pins, which engage in recesses, preferably in the form of holes, in the rotor and couple the rotor in a force-fitting manner to that part of the drive that accommodates the at least one cushion-like element, wherein the engagement elements and recesses are formed such that they allow the wobbling movements or tilting movements of the rotor. In the simplest case, it is sufficient for the diameter of the holes, which extend preferably parallel to the rotational axis of the rotor, to be selected to be slightly larger than the outside diameter of the pins. Since positioning accuracy of about half of one degree is usually sufficient for the rotor, a corresponding clearance between the pins and the holes is readily acceptable.

In this case, the hole for the pin can be configured as a hole, in particular a stepped hole, that widens from the foot of the pin in the direction of the tip of the pin, wherein the inside diameter of the hole at the foot of the pin is only slightly greater than the outside diameter of the pin, that good positioning of the pin is achieved on the one hand, but on the other hand sufficient angular mobility of the pin is ensured. This is because, as a result of the hole widening in the direction of the pin tip, the upper region of the pin is not limited within a region of the acceptable and necessary pivoting movement or wobbling movement.

According to one configuration of the invention, the stator can consist of a metal body on which the port connections are formed and which accommodates a glass or ceramic insert part on which the stator end face is formed. This provides the advantage that the stator end face is also formed from a harder material, wherein the port connections can be formed in a simple, conventional manner in the metal part. Of course, in this case, a sufficient sealing action should be ensured between the two parts, in particular in the region of the transition of the ducts forming the ports from the metal part into the part consisting of the harder material. This sealing action can be achieved for example by adhesive bonding of the two parts or by the interposition of one or more sealing elements, wherein the two stator parts are pressed together by the pressing together of the stator and rotor, such that a sealing action is ensured as a result. Rather than one or a plurality of separate sealing elements, a thin plastics layer can be applied and thus firmly connected to one of the two parts at least in portions between the metal body and the insert part.

A suitable material for such sealing elements or sealing plastics layers is in particular polyether ketone, preferably PEEK.

Preferably, however, the sealing takes place via a plug unit which is inserted into the relevant port 118 and is screwed to the latter, wherein the capillary tip extends into the region of the insert part and provides sealing here.

According to a preferred embodiment, a hard, friction-reducing coating, preferably made of amorphous carbon (DLC coating), is applied to the stator end face and/or the rotor end face. Such a layer brings about a reduction in friction at the contact face between the rotor and stator.

Such a coating made of amorphous carbon can in particular be applied by plasma enhanced chemical vapor deposition (PECVD). By way of this process, a very uniform coating can be achieved, such that finishing is no longer required. A very good combination has been found to be the application of such a DLC coating to the end face of a ceramic rotor or stator or a part thereof.

According to one configuration of the invention, the stator end face can be formed in a planar manner in the region of contact with the rotor end face and the rotor end face can be formed in a slightly domed manner in the region of contact with the stator end face, or vice versa, in order to reduce the excessive increase in surface pressure in the peripheral region of the contact face. As a result, the amount of pressure force can be reduced, since the pressure force is distributed more uniformly over the contact face between the rotor and stator. Thus, at a particular necessary surface pressure at the contact face in the region of the port cross sections and grooves, the pressure force necessary for the production thereof can be reduced. In addition, on account of a reduced surface pressure in the peripheral region of the end face of the stator or rotor, wear is reduced.

BRIEF DESCRIPTION OF THE DRAWINGS

The invention is explained in more detail in the following text with reference to an exemplary embodiment illustrated in the drawing, in which.

DETAILED DESCRIPTION OF EMBODIMENTS

Figure 3:
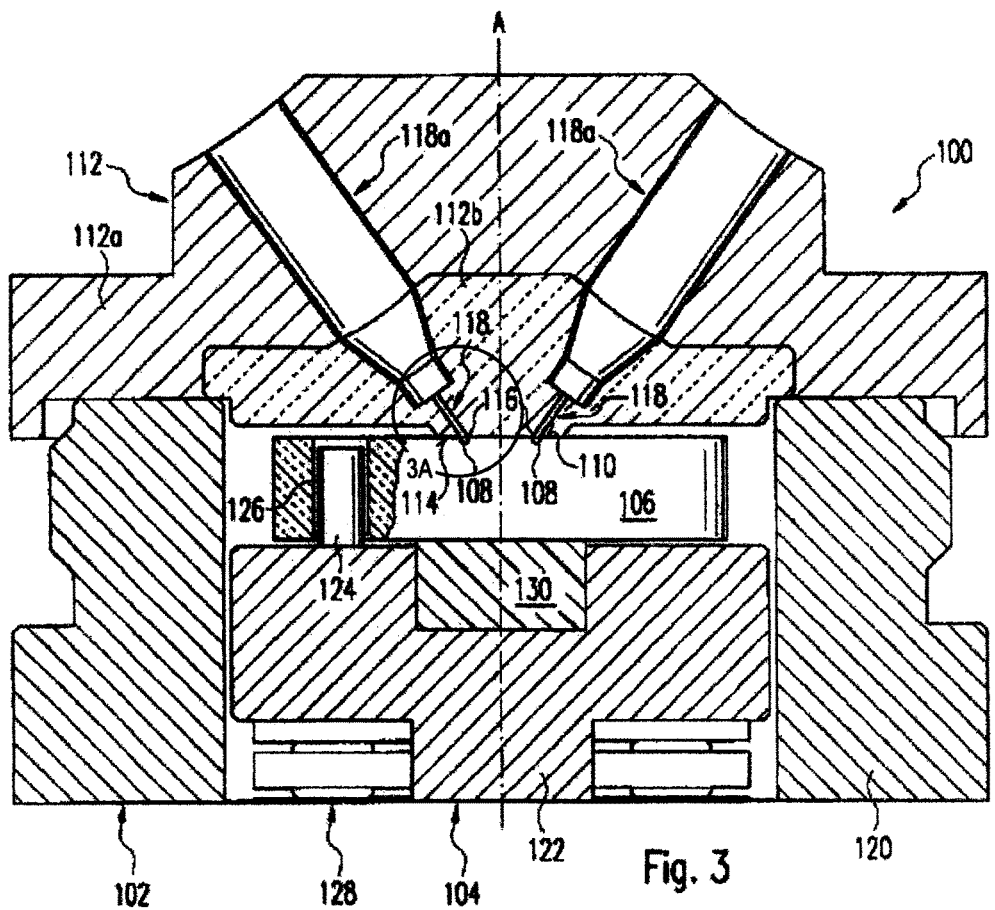
FIG. 3 shows a schematic sectional illustration of a high-pressure switching valve according to the invention.

The high-pressure switching valve 100 illustrated schematically in FIG. 3 consists of a not fully illustrated housing 102 in which there is arranged an only partially illustrated drive 104 which drives a rotor 106 in rotation about the axis A. The drive may be for example an electric-motor-powered drive, in particular a stepping motor, which can be controlled into predetermined switching positions by a control unit (not illustrated in more detail). In this case, of course, not only the predetermined switching positions can be actuated but also the rotational speed or the time profile of the rotational speed.

The rotor 106 of the switching valve 100, in the rotor end face 110 of which one or a plurality of grooves 108 are provided, interacts with a stator 112 which has a stator end face 114 in which port opening cross sections 116 of a plurality of ports 118 formed in the stator 112 open in the manner described at the beginning. The in each case other ends of the ducts forming the ports 118 are connected to only partially illustrated port connections 118a which provide for example a screw connection for connecting high-pressure capillaries. These may accommodate for example a capillary (not illustrated) which extends into the front, narrowed region of the relevant port connection 118a and is pressed against the latter in a sealing manner, for example by means of a plug part that can be screwed into the region 118a.

Figure 1:
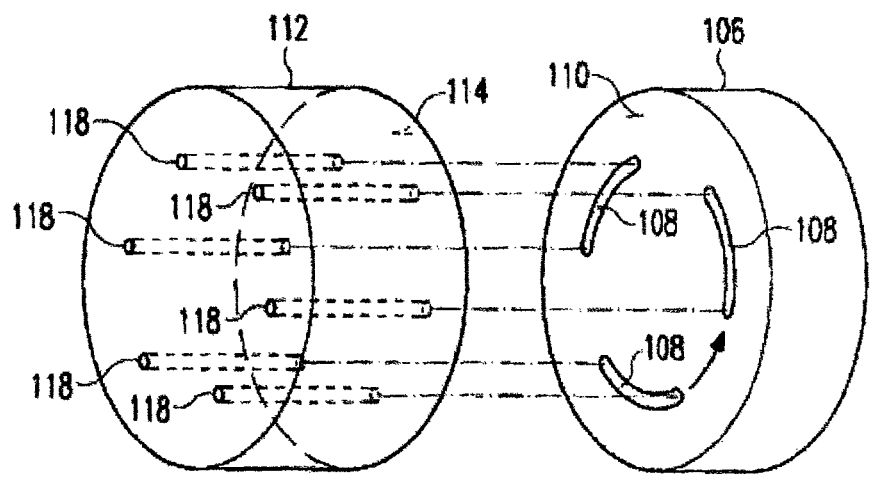
FIG. 1 shows a schematic perspective exploded illustration of a rotor and of a stator of a high-pressure switching valve according to the prior art.
Figure 2:
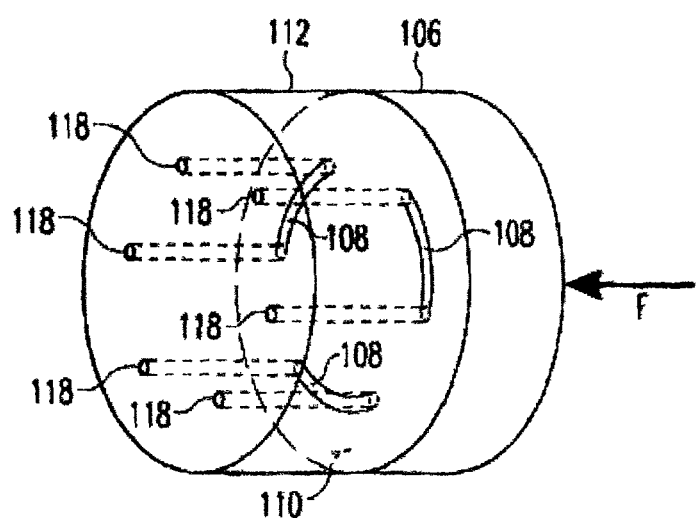
FIG. 2 shows a schematic perspective of a rotor, interacting with a stator, of the high-pressure switching valve from FIG. 1.

The basic mode of operation of the high-pressure switching valve 100 illustrated in FIG. 3 corresponds to the principle illustrated with reference to FIGS. 1 and 2, and so reference can be made to the explanations given above in this regard.

The stator 112 of the high-pressure switching valve 100 illustrated in FIG. 3 can form a part of the housing 102 and be connected for example to a further housing part 120, for example screwed thereto. The housing part 120 may be formed in the manner of a pot such that all of the remaining components of the high-pressure switching valve 100 can be accommodated in the housing part 120, which is illustrated in FIG. 3 only with its upper peripheral region. In particular, the drive 104, which has a rotationally driven part 122, can be arranged in the housing part 120. As is illustrated in FIG. 3, the rotationally driven part 122 of the drive 104 is drivable about the axis A and guided with regard to this movement.

The upper part, facing the rotor 106, of the driven part 122 has a cylindrical shape and has, on its end face facing the rotor 106, a plurality of engagement elements 124 in the form of pins which extend parallel to the axis A. The engagement elements 124 engage in correspondingly formed holes 126 in the rotor 106 which, as illustrated in FIG. 3, can likewise have a cylindrical shape. The engagement elements 124 are arranged preferably along a concentric circle about the axis A. For example, three engagement elements 124 can be provided, which are arranged preferably along the concentric circle. The same applies, of course, to the holes 126 interacting with the engagement elements 124.

As illustrated in FIG. 3, the rotor 106 is pressed by way of its rotor end face 110 against the stator end face 114 of the stator 112. The surface pressure at the contact face of the rotor end face 110 and the stator end face 114 is so great that a sealing action is produced even when the liquid medium is supplied to the high-pressure switching valve 100 at high pressure. To this end, the rotor is acted upon in the axial direction by the part 122 of the drive 104 in the axial direction. To this end, the part 122 of the drive 104 is acted upon axially by a pressure unit 128. This may be a spring unit formed in an annular manner which, as illustrated in FIG. 3, acts upon an annular, rear end face of the part 122. The pressure unit 128 can be supported against the base (not illustrated) of the housing part 120 by way of the other end.

In the case of the embodiment illustrated in FIG. 3, the stator is configured in two parts. An outer part 112a consists preferably of metal, such that the port connections 118a for the ports 118 can be produced in a simple manner, for example by drilling.

An inner stator part 112b, which is accommodated in the outer stator part 112a and on which the stator end face 114 is also formed, can be produced from a hard material, in particular from ceramic. Of course, it is necessary to form the relevant parts of the ducts forming the ports 118 in this ceramic part, said ducts opening into the corresponding port opening cross sections in the stator end face 114.

The use of an inner stator part 112b consisting of hard material instead of a stator 112 consisting entirely of the hard material provides the advantage that the port connections can be produced in simpler manner.

Since the stator end face 114 consists of a hard material, such as ceramic, corresponding wear resistance and stability of the high-pressure switching valve 100 are achieved.

The inner stator part 112b can be pressed into a corresponding recess in the inner side of the outer stator part 112a. However, this is not absolutely necessary. Rather, as illustrated in FIG. 3, the inner stator part 112b can also have on its outer circumference a shoulder by way of which the inner stator part 112b rests on the annular end face of the housing part 120. Since the stator 112 is connected by way of its outer stator part 112a to the housing part 120, for example is screwed thereto, in the two-part configuration illustrated in FIG. 3, the inner stator part 112b is held securely between the outer stator part 112a and the end side of the housing part 120.

In addition, the inner stator part 112b is fixed securely in the housing by the application of a high-pressure force which is produced by the pressure unit 128 and is transmitted to the inner stator part 112b by the driven part 122 of the drive 104 and the rotor 106.

It would thus not be absolutely necessary for the stator part 112b to be supported on the housing part 120. Rather, the stator part 112b can also be securely fixed in its position just by the pressure force which is exerted via the rotor 106 onto the stator 112.

The ensuring of a sufficiently precise radial position of the stator part 112b or of the stator 112 is ensured by the recess in the outer stator part 112a, into which recess the inner stator part 112b can be inserted with a precise fit, and by the sufficiently exact radial positioning of the stator as a result of the connection to the housing part 120.

In order to achieve high wear resistance and stability, the rotor 106 of the high-pressure switching valve 100 is likewise produced from a hard material, preferably from ceramic. As a result, a rotor end face 110 and a stator end face 114, which each consist of hard material, interact with one another. Since such hard materials have only extremely low elasticity, which is not sufficient to compensate usual tolerances during the manufacturing and mounting of the high-pressure switching valve, in particular tilting of the rotational axis A of the rotor with respect to the normal to the stator end face 114, given a conventional construction of the high-pressure switching valve there would be a high risk that, at the high necessary surface pressure or the high pressure force which is exerted via the rotor 106 onto the stator 112, the stator end face 114 and/or the rotor end face 110 would be damaged, in particular during the rotary movement of the rotor 106.

For this reason, the underside, i.e. the end side, remote from the rotor end face 110, of the cylindrical rotor 106 is not acted upon directly by the end face of the rotationally driven part 122 of the drive 104, but via a cushion-like element 130. The cushion-like element 130 consists of a sufficiently soft and elastic material to allow a wobbling movement or tilting movement of the rotor 106 during its movement about the axis A. However, the material of the cushion-like element 130 is sufficiently rigid to transmit the pressure force necessary for the sealing action at the contact face between the rotor 106 and stator 112. The cushion-like element 130 is accommodated in an axial recess in the rotationally driven part 122 of the drive 104 in the embodiment illustrated in FIG. 3 and projects by way of its top side slightly beyond the upper end face of the part 122. The material and this protrusion of the cushion-like element 130 should be selected such that, even when the full pressure force is transmitted on to the rotor 106, the element 130 is not compressed to such an extent that the rotor 106 rests with its rear end side flat against the end face, facing it, of the part 122. This is because, in this case, the necessary wobbling movements of the rotor 106 would be blocked.

The material of the element 130 can be a sufficiently firm or hard and yet elastic plastics material, for example a polyether ketone. In particular, the part 130 can consist of PEEK. Of course, the coupling between the driven part 122 and the rotor 106 by means of the engagement elements 124 and the recesses or holes 126 interacting therewith also has to be configured such that the wobbling movements are enabled to a sufficient degree. To this end, the inside diameter of the holes 126 can be selected to be larger by a corresponding degree than the outside diameter of the engagement elements or pins 124. Such a clearance between the engagement elements 124 and the recesses 126 is acceptable also with regard to sufficiently exact angular positioning of the rotor 106.

Figure 4:
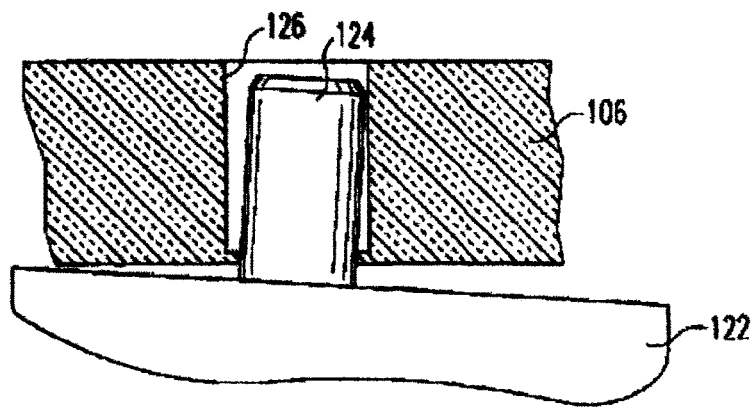
FIG. 4 shows an enlarged illustration of the region of the rotationally conjoint connection between the rotor drive and the rotor from FIG. 3.

As can be seen from the enlarged detail according to FIG. 4, sufficiently exact angular positioning about the axis A is achieved in that the recesses 126 in the lower region, that is to say in the foot region of the engagement element 124, have a smaller inside diameter than in the front region of the engagement element 124. The inside diameter of the recess 126 has to be selected in this region (relatively small axial height) such that the required accuracy of the angular positioning of the rotor about the axis A is achieved, but the ability to wobble about a desired angular range remains. This positioning accuracy has to be in an order of magnitude of about half of one degree. This is sufficient in order to ensure a secure connection between the ports 118 and the grooves 108 or complete isolation of the ports 118 from the grooves 108 in the predetermined switching positions of the high-pressure switching valve 100.

Of course, the desired wobbling movement of the stator 106 when hard materials are used for the rotor and stator can also be achieved by means of other constructions. For example, instead of a single axially arranged cushion-like element 130, a plurality of cushion-like elements arranged around the circumference of a coaxial circle in the end face of the part 122 may also be used. Instead of a cushion-like element made of plastics material, it is likewise possible to use other means that ensure corresponding movability of the rotor 106, for example spring elements made of metal (spiral springs, plate springs, solid-body joints etc.).

The construction, illustrated in FIGS. 3 and 4, of a high-pressure switching valve 100 thus ensures, via the allowing of necessary wobbling movements of the rotor 106, that the rotor end face 110 rests in a planar manner against the stator end face 114 with a surface pressure which is as uniform as possible over the entire contact face in every angular position of the rotor 106 and also during its rotary movement.

In order to reduce the friction between the stator end face 114 and the rotor end face 110, the use of what is known as a DLC coating on one of the two surfaces or on both surfaces has been found to be advantageous.

Although such a coating on a hard surface of a stator is known in the prior art, in this case an element made of a synthetic resin is used as rotor. Since the interaction of different materials and coatings on surfaces made of particular materials frequently entails surprising effects for reducing friction and for creating surfaces which are as wear-resistant as possible, it was thoroughly surprising that such a DLC coating is advantageous both for the stator 112 and for the rotor 106 when hard materials, in particular ceramics, are used.

Such a DLC layer was applied using a plasma enhanced chemical vapor deposition (PECVD). As a result, an extremely uniform coating with a constant thickness was produced. The application of such a DLC layer to a ceramic surface which is as planar as possible thus results in an extremely planar and smooth stator end face 114 or rotor end face 110.

Figure 3A:
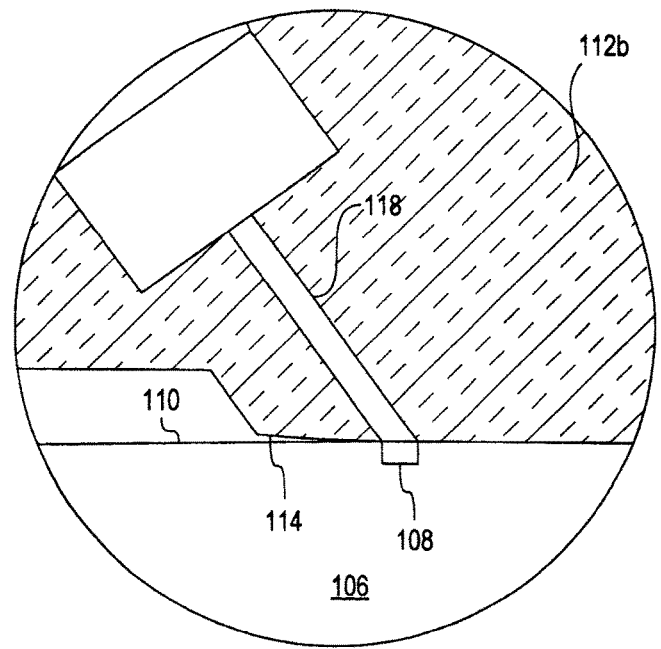
FIG. 3A is an enlarged detail 3A of the high-pressure switching valve of FIG. 3.

A further improvement in the region of the contact face between the rotor 112 and the stator 106 can be achieved in that one of the two surfaces, in the construction according to FIG. 3 preferably the stator end face 114, is formed in a slightly domed manner. In particular, the stator end face 114 may be formed in a planar manner in the region of contact with the rotor end face 110 and the rotor end face 110 is formed in a slightly domed manner in the region of contact with the stator end face 114, or in that the rotor end face 110 may be formed in a planar manner in the region of contact with the stator end face 114 and the stator end face 114 is formed in a slightly domed manner in the region of contact with the rotor end face 110, or both the rotor end face 110 and the stator end face 114 may be formed in a slightly domed manner in the region of contact with the in each case other end face (see FIG. 3A). As a result, the effect of the excessive increase in the surface pressure in the outer peripheral region of the contact face can be reduced.

Figure 5:
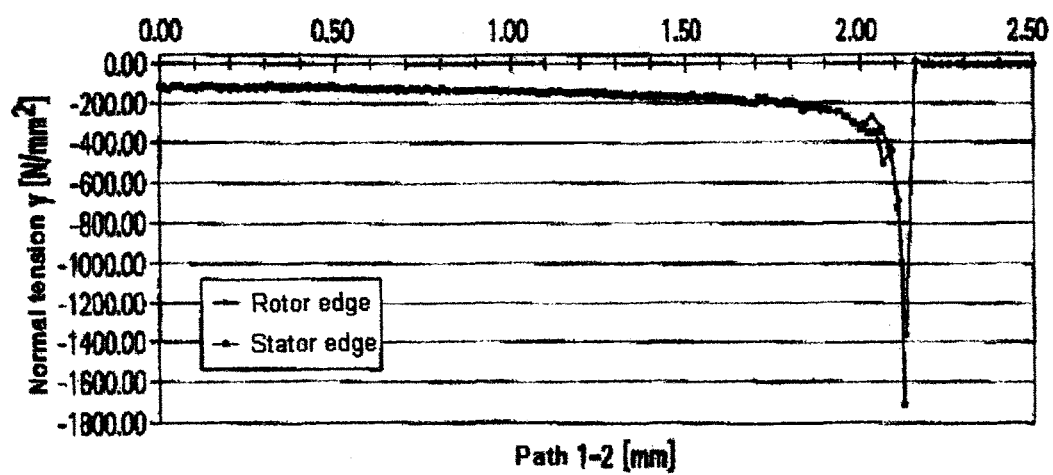
FIG. 5 shows a diagram for explaining the excessive increase in the surface pressure in the peripheral region of the contact face between the rotor and stator of the high-pressure switching valve from FIG. 3.

FIG. 5 shows a simulation for the surface pressure (the slight deviations for the curves "rotor edge" and "stator edge" result from numeric inaccuracies which are produced for example by the definition of the boundary conditions) without a domed configuration of the stator end face 114. As can be seen from FIG. 5, an extreme excessive increase in the surface pressure is produced in the peripheral region. Since the force for creating the surface pressure is determined as an integral over the profile of the surface pressure and the radius, it is clear from FIG. 5 that a quite considerable part of the axial pressure force "is lost" in the outer peripheral region and cannot contribute to producing a sufficient sealing action in the radially inner region of the contact face between the rotor end face 110 and stator end face 114, in which the port opening cross sections 116 and the grooves 108 are located.

A slightly domed formation (optionally with different radii) of the stator end face 114 can thus contribute firstly to reducing the necessary pressure force F between the rotor and stator (in order to ensure a sealing action) and secondly to avoiding extremely high surface pressures in the radial peripheral region, which may in this region result in increased wear or in destruction of the surfaces and possibly of the entire parts.

Thus, the invention creates a high-pressure switching valve which has improved wear resistance and stability on account of the use of hard and optionally also brittle materials for the rotor and stator in conjunction with the allowing of wobbling movements for the rotor. An additional coating on one or both of the end faces of the rotor and/or stator can have an additional advantageous effect in relation to the wear resistance and the frictional action between the two parts. A domed formation on one of the two end faces results in further reduced surface pressure in the radial peripheral region and thus likewise increases the wear resistance.

Of course, the invention is not limited to the exemplary embodiment illustrated in FIG. 3. In addition to the further possibilities already outlined above, reference is made to the fact that the stator can of course also be mounted such that it can carry out a wobbling movement. In this case, the rotor can be structurally formed in the usual manner.

In order to achieve appropriately flexible mounting of the stator, the embodiment according to FIG. 3 can be altered for example such that the stator 112 is not connected firmly to the housing part 120 but rather via elastic, for example again cushion-like elements provided between the underside of the outer stator part 112a and the annular end face of the housing part 120. Thus, the entire stator 112 can be tilted with respect to the housing part 120. Radial positioning and axial fastening of the stator 112 to the housing part 120 can then take place for example by means of a further connecting element. This can be configured for example as an annular nut which can be screwed to the part 120 and which acts by way of an upper shoulder upon the upper side of the stator 112 and presses the latter in the axial direction onto the housing part 120.

Furthermore, a thin layer or a separate thin element can also be provided between the inner stator part 112b and the outer stator part 112a, said thin layer or separate thin element being elastically or plastically deformable such that tolerances between said parts or irregularities on the surfaces thereof can be compensated. In addition, a sealing action at the transition between the ducts forming the ports 118 can be achieved here at the transition from the part 112b to the part 112a or vice versa.

The thickness of the layer or of the separate part and the elasticity thereof can also be selected such that, with the sealing action being maintained, the part 112b is mounted with wobbling action in the part 112a. In this case, however, the part 112b should not, as illustrated in FIG. 3, be supported on the housing part 120 but has to be accommodated in the part 112a in a movable manner (but in a manner fixed sufficiently precisely with regard to transverse movements in the plane of the contact face).

The rotor can be formed in a two-part form both in such an embodiment and in the embodiment illustrated in FIG. 3, wherein an inner part that forms the rotor end side and is made of hard material, such as glass or ceramic, is held in an outer part which accommodates this part and is made of softer material, for example plastics material. As a result, in the case of a more complicated geometry for the outer part, it is simpler and cheaper to produce the latter.

Figure 6:
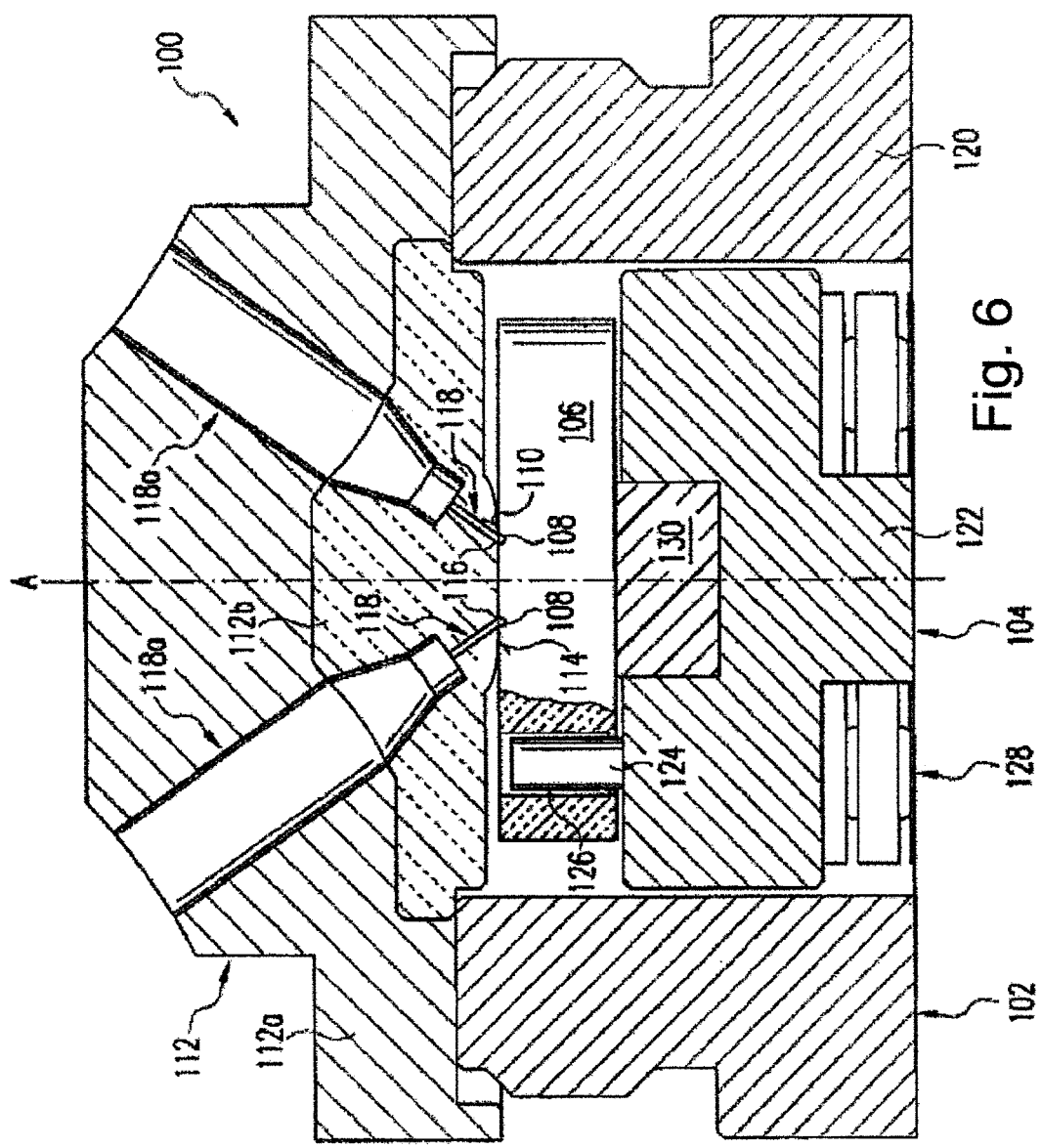
FIG. 6 shows a schematic sectional illustration of a high-pressure switching valve according to another embodiment of the invention.

FIG. 6 shows another embodiment of a high-pressure switching valve having a more pronounced domed region on stator end face 114.

Figure 7:
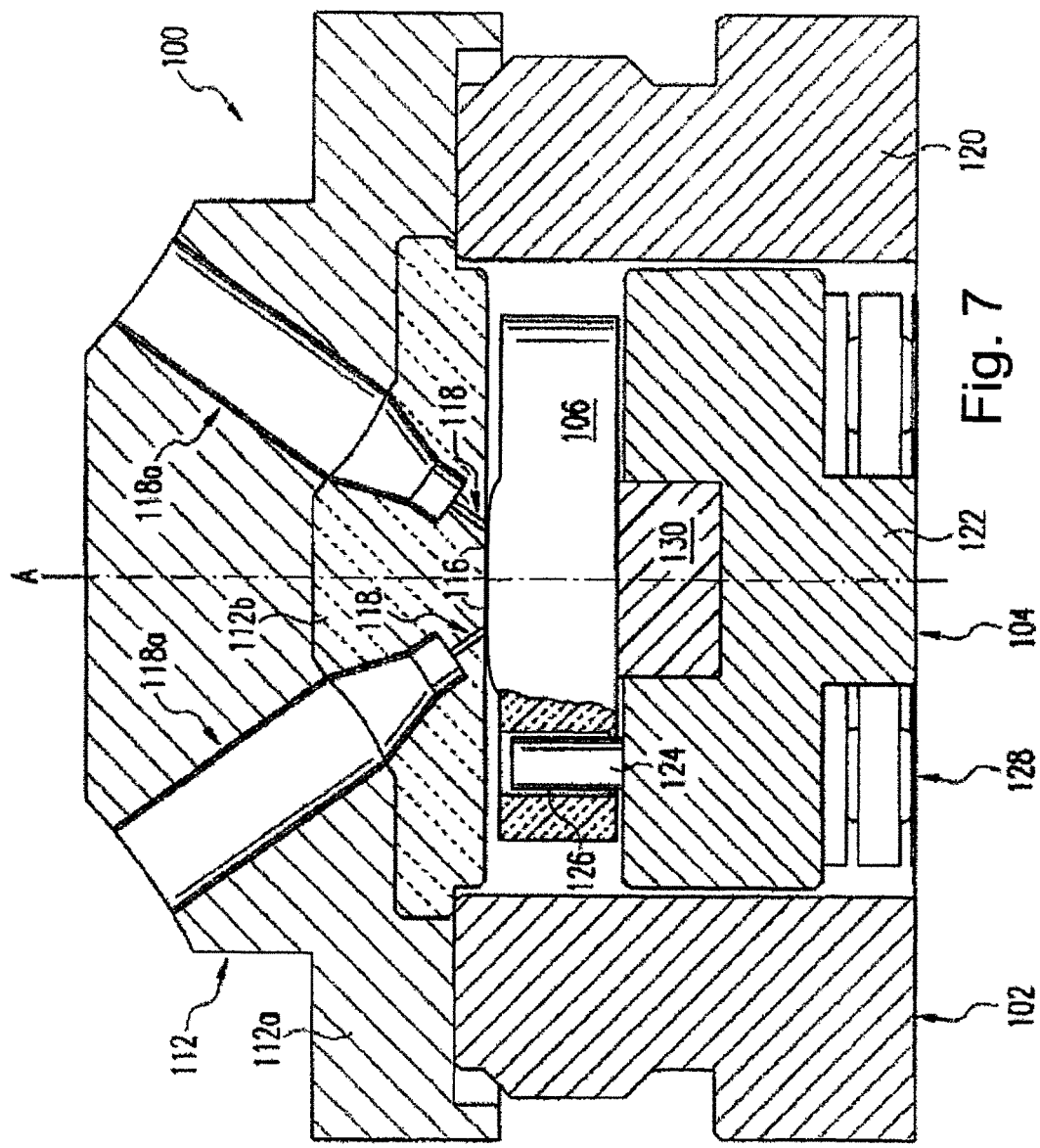
FIG. 7 shows a schematic sectional illustration of a high-pressure switching valve according to yet another embodiment of the invention.

FIG. 7 shows another embodiment of a high-pressure switching valve having a more pronounced domed region on rotor end face 110.

Figure 8:
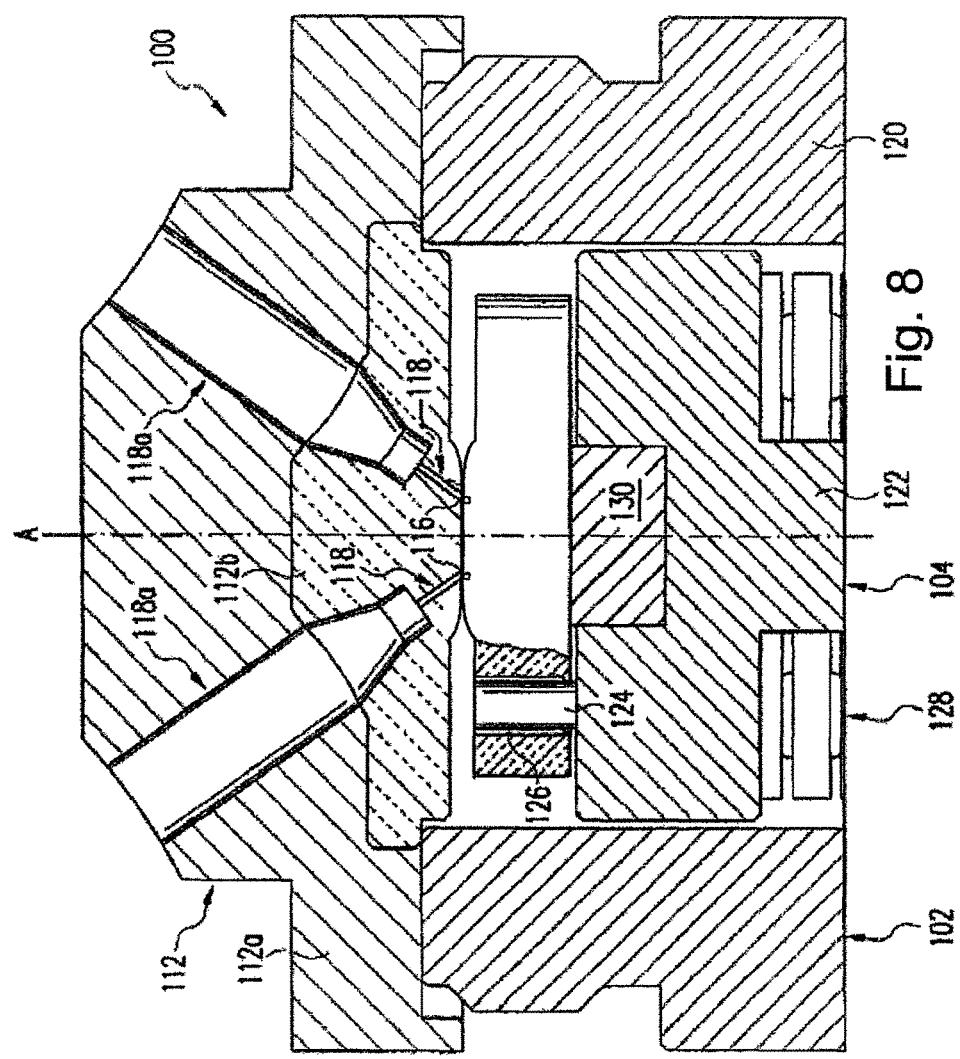
FIG. 8 shows a schematic sectional illustration of a high-pressure switching valve according to yet another embodiment of the invention.

FIG. 8 shows another embodiment of a high-pressure switching valve having a more pronounced domed region on both stator end face 114 and rotor end face 110.

What is claimed is:

1. A high-pressure switching valve for high-performance liquid chromatography, the high-pressure switching valve comprising:
   (a) a stator including a plurality of ports, wherein each port is connected at one end to a port connection and each port having at another end a predetermined port opening cross section at a stator end face of the stator,
   (b) a rotor including a rotor end face, in which the rotor end face presses against the stator end face and in which the rotor end face includes at least one or a plurality of grooves, the rotor configured to have a rotary position with respect to the stator where two predetermined port opening cross sections connect to one of the grooves in a pressure-tight manner,
   (c) wherein the rotor and the stator are pressed together in a sealing manner in a region of contact at the rotor end face and the stator end face,
   (d) the rotor and the stator each comprise a hard material, and
   (e) in that the rotor is configured to wobble or tilt with respect to a rotational axis of the rotor,
   in which the stator end face includes a planar region in the region of contact with the rotor end face, and the rotor end face includes a domed region in the region of contact with the stator end face, or
   the rotor end face includes a planar region in the region of contact with the stator end face, and the stator end face includes a domed region in the region of contact with the rotor end face, or
   the rotor end face includes a domed region in the region of contact with the stator end face and the stator end face includes a domed region in the region of contact with the rotor end face, in which a peripheral region of the region of contact has a reduced surface pressure when applying pressure between the rotor and the stator compared to another high-pressure switching valve that does not have at least one domed region of a stator end face or a rotor end face.

2. The high-pressure switching valve of claim 1, in which each port is a duct.

3. The high-pressure switching valve of claim 1, in which the hard material is selected from the group consisting of a metal, a glass, and a ceramic.

4. The high-pressure switching valve of claim 1, in which a portion of the rotor at a region of the rotor end face is the hard material and a portion of the stator at a region of the stator end face is the hard material.

5. The high-pressure switching valve of claim 1 further comprising: at least one cushion-like element coupled to the rotor that causes the rotor to wobble or tilt with respect to the rotational axis of the rotor.

6. The high-pressure switching valve of claim 5, in which the cushion-like element is sufficiently soft and elastic to allow a wobbling movement and is also sufficiently rigid to generate the pressure force necessary for the sealing manner at the rotor end face and the stator end face.

7. The high-pressure switching valve of claim 5, in which the cushion-like element is a material selected from the group consisting of a polymer material, a polyimide, a polyamideimide, and a polyether ketone.

8. The high-pressure switching valve of claim 5, in which the cushion-like element comprises PEEK.

9. The high-pressure switching valve of claim 5, in which the at least one cushion-like element is disposed in a recessed portion of a rotationally driven part of a drive for the rotor, the rotationally driven part being arranged on a side remote from the rotor end face.

10. The high-pressure switching valve of claim 5, in which the cushion-like element comprises a spring element.

11. The high-pressure switching valve of claim 9, in which the rotationally driven part is coupled to the rotor for conjoint rotation.

12. The high-pressure switching valve of claim 9, in which the rotationally driven part includes a plurality of engagement elements configured to engage in corresponding recesses in the rotor and couple the rotor to the drive.

13. The high-pressure switching valve of claim 12, in which the engagement elements and the recesses are configured to allow wobbling movements or tilting movements of the rotor.

14. The high-pressure switching valve of claim 12, in which the engagement elements comprise pins and the recesses comprise holes.

15. The high-pressure switching valve of claim 14, in which the recesses have a smaller diameter in a foot region of the corresponding engagement element than in a head region of the corresponding engagement element axially adjoining the foot region.

16. The high-pressure switching valve of claim 1, in which the stator comprises:
   a metal body that forms the port connections and
   a glass or ceramic insert part that forms the stator end face.

17. The high-pressure switching valve of claim 16, in which the stator further comprises: a plastic layer at least partially disposed in between the metal body and the insert part.

18. The high-pressure switching valve of claim 17, in which the plastic layer is a material selected from the group consisting of a polyimide, a polyamideimide, and a polyether ketone.

19. The high-pressure switching valve of claim 1, in which the hard material of the rotor end face and the stator end face each comprise an amorphous carbon coating.

20. The high-pressure switching valve of claim 19, in which the amorphous carbon is applied by a plasma enhanced chemical vapor deposition.

* * * * *